United States Patent [19]

James et al.

[11] Patent Number: 4,600,018

[45] Date of Patent: Jul. 15, 1986

[54] ELECTROMAGNETIC MEDICAL APPLICATORS

[75] Inventors: James R. James, Swindon; Reginald H. Johnson, Malvern; Ann Henderson; Mary H. Ponting, both of Swindon, all of England

[73] Assignee: National Research Development Corporation, London, England

[21] Appl. No.: 499,544

[22] Filed: May 31, 1983

[30] Foreign Application Priority Data

Jun. 2, 1982 [GB] United Kingdom ............... 8216129

[51] Int. Cl.$^4$ ........................................... A61N 5/00
[52] U.S. Cl. ....................................... 128/804; 343/787; 343/700 MS
[58] Field of Search .................... 128/804, 399; 219/10.79, 10.81, 10.55 R; 343/700 MS, 787

[56] References Cited

U.S. PATENT DOCUMENTS

| | | | |
|---|---|---|---|
| 2,814,298 | 11/1957 | Argento | 128/804 |
| 3,077,195 | 2/1963 | Folsche | 128/804 |
| 3,811,128 | 5/1974 | Munson | 343/700 MS |
| 4,240,445 | 12/1980 | Iskander et al. | 128/804 |
| 4,312,364 | 1/1982 | Convert et al. | 128/804 |

FOREIGN PATENT DOCUMENTS 458534 12/1936 United Kingdom .
762734 12/1956 United Kingdom .
862646 3/1961 United Kingdom .
1596459 8/1981 United Kingdom .

OTHER PUBLICATIONS

Bahl et al., "Microstrip Loop Radiators . . . ", Conf: 1981 IEEE MTT.S Int. Microwave Symp. Dig., Los Angeles, Ca. pp. 465–467 (Jun. 15–19, 1981).
Bahl et al., "A New Microstrip Radiator . . . ", IEEE Trans. on MTT, vol-MTT-28, No. 12, Dec. 1980, pp. 1464–1468.

*Primary Examiner*—Lee S. Cohen
*Attorney, Agent, or Firm*—William R. Hinds

[57] ABSTRACT

An electromagnetic medical applicator for tissue-heating comprises a single resonant element (1) in contact with one surface of a layer of material (5) whose opposite surface faces the body of a patient (6). The material has a wave-impedance which approximately matches that of the human body and a dielectric constant not less than for a material having unity magnetic permeability which produces this match. In one form the element is a patch resonator (1) on a substrate (2) backed by a ground-plane (3) and overlaid by the layer (5); at least the substrate may include both dielectric and magnetic material in order to combine a desired resonator size-reduction and wave-impedance. In another form a needle-type applicator is coated with the layer of material.

6 Claims, 3 Drawing Figures

ELECTROMAGNETIC MEDICAL APPLICATORS

This invention relates to electromagnetic medical applicators, also known as transducers. Such applicators or transducers have one use in the heating of tissues, either alone or together with radiotherapy or chemotherapy, to treat cancer patients. A review paper describing the technique, by J W Hand, was published in IEE PROC, Vol. 128, Pt A, No 9, December 1981, pp 593–601, entitled "Electromagnetic techniques in cancer therapy by hyperthermia". It has been established that tumours are more prone to damage by heat than are healthy cells. Alternatively it is found that other forms of treatment such as radiotherapy and chemotherapy are more effective if the tumour is preheated selectively.

The applicators of present concern are arranged to radiate electromagnetic radiation which is absorbed by the body tissue with resultant heating. It is desirable that such applicators should be physically small so as to be able to localise the heating as far as possible on small tumours at an early stage of growth. At present only certain frequencies are allocated for this medical work, viz 13,27,41,168,900 and 2450 MHz. At the higher end of this range the radiating element of the applicator can be made suitably small, but at 2450 MHz for example, the radiation only penetrates about 1 cm of tissue. It is therefore desirable in some applications to use lower frequencies, e.g. at 13 MHz the radiation penetrates some tens of cms, and there is a need for physically small applicators for use at these lower frequencies. Additionally, the applicator used to transmit electromagnetic radiation for heating may also serve to receive such radiation as a way of monitoring the tissue temperature (see e.g. K L Carr et al, IEEE, MTT Vol 29, No 3, March 1981, pp256–260), and in such cases also, the applicator should be as small as possible.

Another desirable feature of such applicators is that any impedance discontinuity between the applicator and the surface of the tissue should be minimised in order to avoid reflections and to maximise the flow of electromagnetic radiation into the tissue. For this purpose it is known to place cushions of dielectric material between the body of the patient and the applicator, e.g. deionised water as described by R. Paglioni et al, in Microwave J, Vol 24, No 2, February 1981, pp 71-2, 74-6, 79-80.

In J Microwave Power, Vol 14, No 2, pp 139–144, 1979, J Mendecki et al describe a medical applicator comprising a printed-circuit array of eight dipoles sandwiched between layers of dielectric powder giving a four-fold reduction in resonant frequency over that of the same array in free-space, indicating an effective $\epsilon_r$-value for the powder of about 16; this value of $\epsilon_r$ is undesirably low for good impedance matching to tissue. Moreover the use of an array, as opposed to a single radiating element, has disadvantages for producing a penetrative beam. Since, as already mentioned, attenuation in tissue increases with frequency, at high frequencies the range at which the array forms a beam will result in high attenuation. If in order to reduce the attenuation the resonant frequency of the array is reduced, the dimensions of the array increase accordingly, so that an array with acceptable attenuation becomes too large relative to the human body.

The present invention provides forms of applicators which allow improved impedance matching to the tissue and a controllable reduction in physical size in relation to frequency.

According to the present invention an electromagnetic medical applicator comprises a single radiating element in substantially surface-to-surface contact with one surface of a layer of material whose opposite surface, in use, faces the body of a patient and through which electromagnetic radiation passes into the body, said material having a wave-impedance (where $\mu_r$ and $\epsilon_r$ are respectively the relative magnetic permeability and permittivity of the material) which approximately matches that of human tissue at the operating frequency, the value of $\epsilon_r$ for the material being not less than for a material having $\mu_r=1$ which produces said approximate match.

Preferably, taking into account the efficient supply of power to the applicator, the approximately matching wave-impedance of the material is not less than approximately two-thirds, and not more than approximately one-and-a-half times, the wave-impedance of human tissue at the operating frequency.

Said material may have a value of $\mu_r>1$ at said frequency, preferably by inclusion of a magnetic, e.g. ferrite material, for a reason explained hereafter. Where no such material is included (i.e. $\mu_r=1$), the preferred value of $\epsilon_r$ for the material is related to the value of $\epsilon_r$ for tissue in such a way as to satisfy the aforesiad preferred range of wave-impedances relative to that of tissue; thus for values of $\epsilon_r$ (tissue) of 40,50 and 70, for example, the corresponding values of $\epsilon_r$ (dielectric material only) will be in the ranges 20–80, 25–100 and 35–140 respectively.

Human tissue can be regarded as having an $\epsilon_r$ value of about 40–50 at 9000 MHz and a loss tangent tan $\delta_\epsilon(=\epsilon_r''/\epsilon_r'$ where $\epsilon_r''$ and $\epsilon_r'$ are respectively the imaginary and real parts of $\epsilon_r$) of about 0.5. The $\epsilon_r$ value rises to about 70 as the frequency falls to about 100 MHz. The value of $\mu_r$ for human tissue is unity. Thus, taking a tissue value of $\epsilon_r=40$ by way of example, by interposing betwen the radiating element and the body a material, having $\epsilon_r\approx40$ and $\mu_r=1$, suitably a known ceramic such as strontium zirconate ($\epsilon_r\approx38$), the impedance level $\sqrt{\mu_r/\epsilon_r}$ remains reasonably constant across the interface between the applicator and the body and the radiation passes into the body with minimised reflection at the interface. A material of higher $\epsilon_r$, e.g. rutile (TiO$_2$) having $\epsilon_r\approx100$, may be used by cutting a number of small holes or grooves therein to reduce the total volume of dielectric material and hence the effective value of $\epsilon_r$. These holes or grooves may be used for cooling by ducted air.

The radiating element may, for example, be a conventional patch radiator made of metal foil applied to, or of metallising deposited on, a ceramic substrate backed by a metallic groundplane, with a layer of the aforesaid material overlying the radiating element. The element may be sandwiched between two layers of such material, one carryng the ground-plane. A needle-type applicator may comprise a small-diameter conductor coated with a layer of such material.

As described in UK Patent Application No. 2,013,037A, the physical length of a wire monopole for a given electrical length (the latter being its length as a given number of wavelengths or fractions of a wavelength at a given frequency) can be reduced, relative to its length in free space, by a factor $\sqrt{\mu_r\epsilon_r}$ by coating it with a material, preferably a ferrite, having those values. This size-reduction effect applies to electromagnetic radiators generally and thus enables the radiating elements of the present applicators to be reduced in physical dimensions by this factor relative to what their free-space dimensions would be. For example the effect of sandwiching the aforesaid patch radiator, or coating the small-diameter conductor, in a dielectric material having $\epsilon_r \approx 40$, is to reduce the size of a resonant patch or conductor by $\sqrt{40}$.

If furthermore the dielectric material includes a ferrite having $\mu_r > 1$, but $\sqrt{\mu_r/\epsilon_r}$ is kept constant at $\sqrt{1/40}$ by increasing $\epsilon_r$ in order to maintain the impedance matching, then $40\mu_r = \epsilon_r$ and the size reduction factor becomes $\sqrt{40\mu_r^2} = \mu_r\sqrt{40}$ or $\mu_r$ times better than for dielectric material alone. This allows $\mu_r$ and $\epsilon_r$ to be selected so that $\sqrt{\mu_r\epsilon_r}$ gives a desired size reduction while maintaining the impedance matching to tissue. Such a material can be made for example, by mixing together as powders in suitable proportions a ceramic dielectric material such as barium titanate ($\epsilon_r \approx 5000$) and a ferrite material such as the nickel-zinc ferrite Neosid F29 ($\mu_r \approx 10$) in appropriate proportions and hot-pressing the mixture to form a solid.

To enable the nature of the present invention to be more readily understood, attention is directed, by way of example, to the accompanying drawings wherein.

Figure 1:
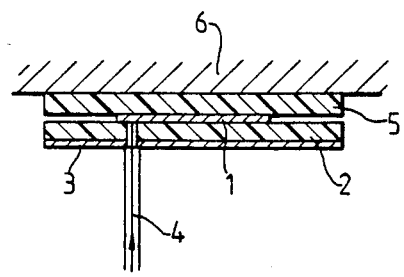
FIG. 1 is a diagrammatic sectional elevation of a planar applicator in contact with a body.
Figure 2:
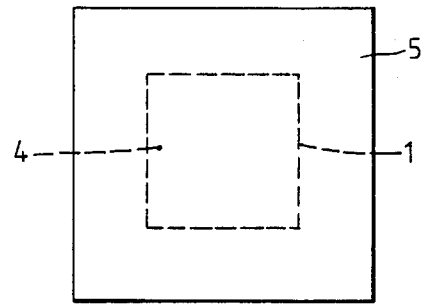
FIG. 2 is a plan view of the applicator of FIG. 1.

In FIGS. 1 and 2 the applicator comprises a conventional square patch radiator, or resonator 1 of metallising deposited on a ceramic substrate 2 backed by a metallised ground-plane 3. The patch is energised by a coaxial connection whose inner conductor 4 extends through ground-plane 3 and substrate 2 to contact radiator 1. Overlying radiator 1 is a layer of ceramic material 5 of the same composition as substrate 2 (the air-gap between them outside the radiator is shown exaggerated for clarity), and the structure suitably is held in a shallow metal tray-like enclosure (not shown) whose rim is flush with the outer surface of layer 5, by small nylon screws countersunk in layer 5 near its corners and extending through the base of the "tray". Other retaining arrangements may be used, e.g. using adhesives. The above-described applicator is shown in intimate contact with the surface of a human body 6 which is to be locally heated by electromagnetic radiation from the radiator 1.

In accordance with one form of the invention the substrate 2 and the layer 5 are each made of a ceramic dielectric material, suitably strontium zirconate having $\epsilon_r \approx 38$, and are suitably about 2 mm thick. For operation as a resonant half-wave patch radiator at 900 MHz, the radiator 1 is suitably 23 mm square; the substrate 2 and layer 5 are suitably 50 mm square. It will be observed that the 23 mm dimension of radiator 1 corresponds approximately to $1/\sqrt{38}(\approx 0.16) \times$ the free-space half-wavelength at 900 MHz ($\lambda_0 \approx 33.4$ cm).

In accordance with another form of the invention, the simple dielectric material of substrate 2 and layer 5 is replaced by a material having a higher value of $\epsilon_r$ and also a value of $\mu_r$ greater than 1, such that $\epsilon_r \approx 40\mu_r$, e.g. $\epsilon_r \approx 80$ and $\mu_r \approx 2$. A mixed ferrite/dielectric material capable of providing such values has been described earlier in the present Application. The impedance, $\sqrt{2180}$, thereby remains unchanged at $\sqrt{1/40}$ for matching purposes, but the size-reduction factor is now increased by a factor 2 to $\approx 0.075$, thereby allowing the above-given length of 23 mm to be halved.

The thickness of layer 5 is not critical but should be more than some minimum since it contains the near field of the radiator 1 and then matches into the load constituted by body 6. A far-field radiation pattern at the tissue surface is desirable to avoid hot spots which can arise from near-field heating. Alternatively, far-field conditions at the tissue surface can be obtained, with a layer 5 insufficiently thick to produce a far-field pattern at its outer surface, by interposing a distilled-water bolus in a suitable thin-walled container (not shown) between this layer and the tissue surface; this increases the distance between the radiator 1 and the tissue surface sufficiently for the far-field pattern to develop, while approximately maintaining the required impedance-matching conditions. The thickness of substrate 2 scales approximately with $\sqrt{\mu_r\epsilon_r}$; it is determined by design requirements for input impedance and efficiency (loss), but, as is known, should not exceed some approximate thickness otherwise unwanted modes can occur in the substrate. The criterion is $H/\lambda_0 < 1/(4\sqrt{\mu_r\epsilon_r})$ where h is the substrate thickness. Layer 5 should not be less thick than substrate 2 where both are of the same material.

It is not essential for radiator 1 to be energised at its resonant frequency for the advantages of the present invention to be achieved, but matching and loss become difficulties off-resonance. Nor need the radiator have the particular configuration (square) shown, e.g. it may be rectangular or circular. A quarter-wave resonant radiator may be used. Where only impedance-matching is desired, without optimum size-reduction, only the layer 5 need have the required $\sqrt{\mu_r/\epsilon_r}$ value, it is only layer 5 which provides the impedance matching, the characteristics of substrate 2 primarily determining the size-reduction factor. So long as $\sqrt{\mu_r\epsilon_r}$ for substrate 2 is $\geq \sqrt{\mu_r\epsilon_r}$ for layer 5, then the presence of layer 5 does not greatly affect ($<25\%$) the radiator dimensions for resonance. Hence a matching layer 5 containing no ferrite may be used in conjunction with a substrate 2 containing ferrite.

Figure 3:
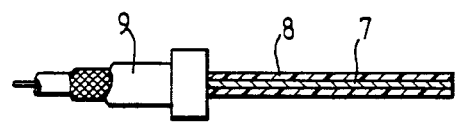
FIG. 3 is a sectional elevation of a needle-type applicator.

FIG. 3 shows a needle-type applicator for insertion into the body. It comprises a small-diameter circular conductor 7 coated with a layer of dielectric, or preerably ferrite/dielectric, material 8 as described with reference to FIGS. 1 and 2. In use, the outer surface of layer 8 contacts the body surface and matches its impedance. The conductor 7 is energised via a coaxial feed 9 and may operate in a resonant mode, e.g. as a monopole or dipole, or in a non-resonant mode. In either mode its electrical length (as hereinbefore defined) as seen by the input from feed 9 is greater than its physical length by the factor $\sqrt{\mu_r\epsilon_r}$.

The present invention can of course be used at frequencies other than 900 MHz, in particular at much lower frequencies in order to obtain the benefit of reduced attenuation in the tissue. The lower the frequency, the more significant becomes the obtainable size-reduction in the resonant radiator.

We claim:

1. An electromagnetic medical applicator comprising:
    a single patch resonator on a substrate backed by a ground-plane, and electrical input connection means to said resonator and ground-plane;
    said resonator being in substantially surface-to-surface contact with a layer of material whose opposite surface, in use, faces the body of a patient and through which electromagnetic radiation passes into the body, said material having a wave-impedance $\sqrt{\mu_r/\epsilon_r}$, where $\mu_r$ and $\epsilon_r$ are respectively the relative magnetic permeability and permittivity for the layer material, which approximately matches that of human tissue at the operating frequency, the value of $\epsilon_r$ for the material being not less than for a material having $\mu_r=1$ which produces said approximate match;

at least said substrate containing both dielectric and magnetic material (a material having $\mu_r<1$) and said substrate having a resultant value of $\sqrt{\mu_r\epsilon_r}$ about equal to or greater than that of said layer, whereby to reduce the surface dimensions of said patch resonator at a predetermined input frequency relative to those dimensions in the absence of said magnetic material.

2. An applicator as claimed in claim 1 wherein the approximately matching wave-impedance of the large material is not less than approximately two-thirds, and not more than approximately one-and-a-half times, the wave-impedance of human tissue at the operating frequency.

3. An applicator as claimed in claim 2 wherein said layer is sufficiently thick to allow a far-field radiation pattern to develop at said opposite surface.

4. An applicator as claimed in claim 1 wherein the surface dimensions of said patch resonator, in conjunction primarily with the resultant value of $\sqrt{\mu_r\epsilon_r}$ for the substrate, are such as to make it act as a half-wave resonator at said predetermined input frequency.

5. An applicator as claimed in claim 4 wherein the approximately matching wave-impedance of the layer material is not less than approximately two-thirds, and not more than approximately one-and-a-half times, the wave-impedance of human tissue at the operating frequency.

6. An applicator as claimed in claim 5 wherein said layer is sufficiently thick to allow a far-field radiation pattern to develop to said opposite surface.

* * * * *